United States Patent
Brandt et al.

(10) Patent No.: US 7,820,434 B2
(45) Date of Patent: Oct. 26, 2010

(54) APPARATUS FOR RECONSTITUTING BONE WITH BIOLOGICAL FLUIDS PRIOR TO SURGICAL IMPLANTATION

(75) Inventors: Robert Brandt, Ft. Myers, FL (US); Michael Buzenius, Naperville, IL (US)

(73) Assignee: Orogen Biosciences, Inc., Ft. Myers, FL (US)

(*) Notice: Subject to any disclaimer, the term of this patent is extended or adjusted under 35 U.S.C. 154(b) by 725 days.

(21) Appl. No.: 11/373,721

(22) Filed: Mar. 10, 2006

(65) Prior Publication Data
US 2006/0154231 A1 Jul. 13, 2006

Related U.S. Application Data

(62) Division of application No. 10/115,623, filed on Apr. 4, 2002, now abandoned.

(51) Int. Cl.
*C12M 1/00* (2006.01)
*A61B 19/00* (2006.01)
*B65D 81/20* (2006.01)

(52) U.S. Cl. .............. 435/308.1; 435/297.2; 435/293.1; 422/292; 604/406; 604/410; 623/919; 206/439; 206/524.8

(58) Field of Classification Search .............. 435/297.2, 435/293.1, 308.1; 604/406, 410; 623/915, 623/919, 920, 923; 422/292; 206/524.8, 206/438, 439
See application file for complete search history.

(56) References Cited

U.S. PATENT DOCUMENTS

| 4,036,698 | A | * | 7/1977 | Bush et al. ................ 435/31 |
| 4,185,623 | A | | 1/1980 | Volkov et al. |
| 4,292,405 | A | * | 9/1981 | Mascoli et al. ............. 435/31 |
| 4,994,030 | A | | 2/1991 | Glowczewskie et al. |
| 5,531,791 | A | | 7/1996 | Wolfinburger, Jr. |
| 6,159,246 | A | | 12/2000 | Mendes et al. |
| 6,613,278 | B1 | | 9/2003 | Mills et al. |
| 6,648,133 | B1 | | 11/2003 | Blaschke et al. |
| 6,649,072 | B2 | | 11/2003 | Brandt et al. |
| 7,198,150 | B1 | | 4/2007 | Blaschke et al. |

FOREIGN PATENT DOCUMENTS

JP 2001095557 A * 4/2001

* cited by examiner

*Primary Examiner*—William H Beisner
(74) *Attorney, Agent, or Firm*—Laura G. Barrow

(57) ABSTRACT

A novel apparatus and device is described for reconstituting a bone sample with a biological fluid, such as concentrated plasma or saline solutions, for example, prior to surgical implantation into a patient. In particular, the invention comprises, in certain aspects, a container in which a bone sample may be reconstituted with the desired fluid by applying a vacuum within the container, thereby driving the fluid into the bone for complete, or near complete, permeation of the fluid into the interstices of the bone sample prior to surgical implantation.

17 Claims, 1 Drawing Sheet

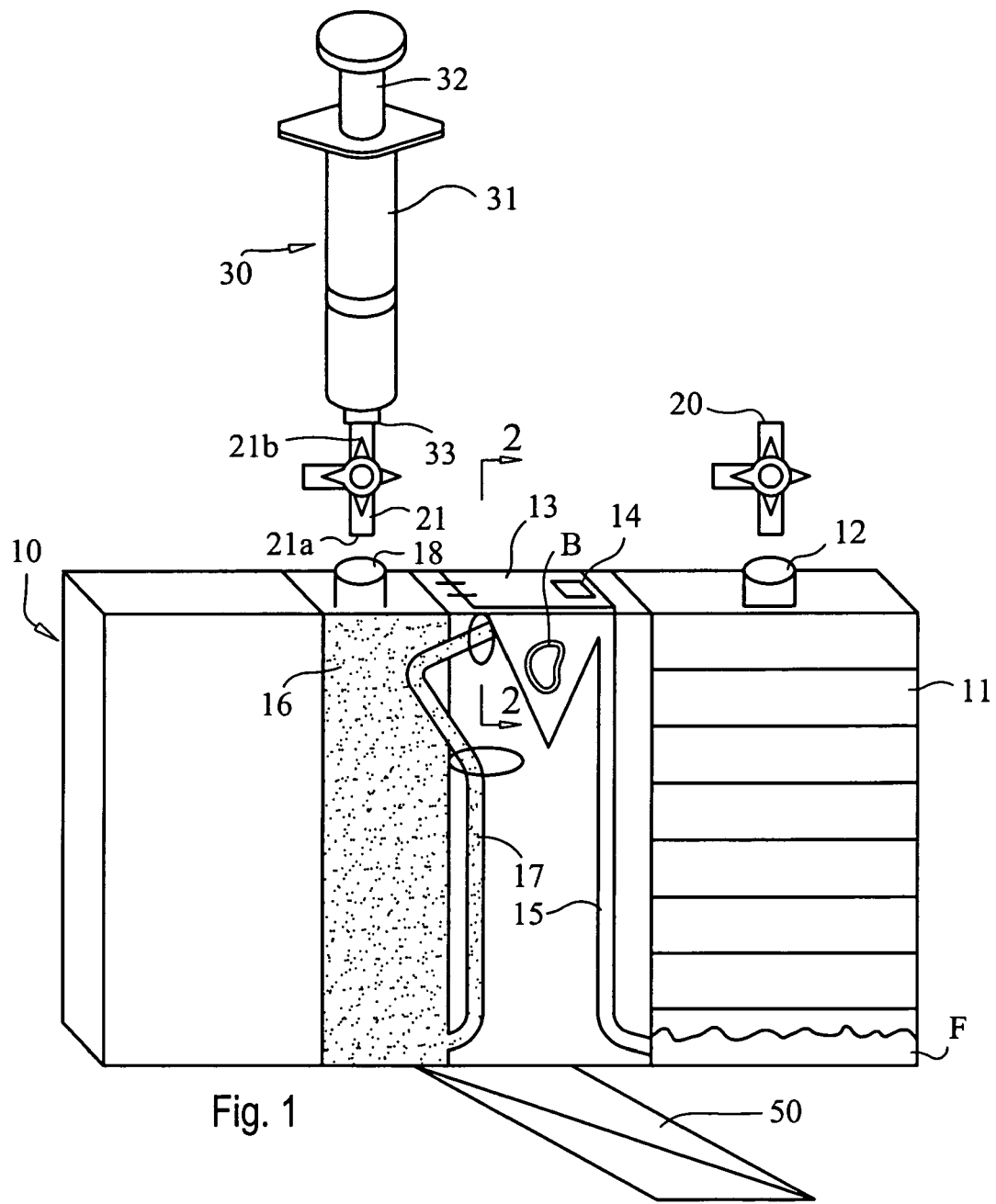
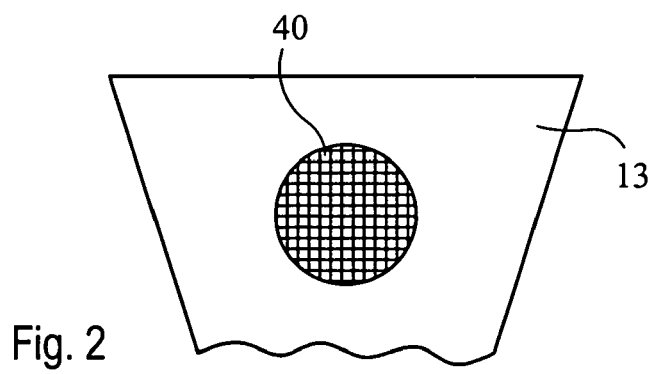

APPARATUS FOR RECONSTITUTING BONE WITH BIOLOGICAL FLUIDS PRIOR TO SURGICAL IMPLANTATION

This is a divisional application of Ser. No. 10/115,623, filed Apr. 4, 2002, now abandoned and incorporated herein by reference in its entirety.

BACKGROUND AND SUMMARY OF THE INVENTION

In certain orthopedic and neurosurgical procedures, cadaveric bone is used to repair or replace damaged bone structures, such as the spine, for example. Tissue banks currently provide cut and processed cadaveric bone for use as struts and fillers in various orthopedic procedures. In many patients, unfortunately, the implanted bone fails to fuse with the patient's own bone. One solution to this problem is to add a stimulant or human growth factor to enhance the probability of fusion. Current procedures for reconstituting cadaveric bone with concentrated growth factor fluids, for example, include simply soaking the bone in the solution for a certain period of time. Notwithstanding its simplicity, this method can be time-consuming and fail to completely permeate the interstices of the bone sample with the fluid.

The present invention is directed to a novel apparatus and device for reconstituting a bone sample with a biological fluid, such as concentrated plasma or saline solutions, for example, prior to surgical implantation into a patient. In particular, the invention comprises, in certain aspects, a container in which a bone sample may be reconstituted with the desired fluid by applying a vacuum within the container, thereby driving the fluid into the bone for complete, or near complete, permeation of the fluid into the interstices of the bone prior to surgical implantation.

BRIEF DESCRIPTION OF THE DRAWINGS

FIG. 1 is a perspective view of one embodiment of the apparatus of the present invention.

FIG. 2 is a sectional view taken along lines 2-2 of FIG. 1 showing the air permeable membrane inserted within or between the vacuum tube and the bone chamber of the preferred embodiment of the present invention.

DETAILED DESCRIPTION OF THE PREFERRED EMBODIMENTS

Referring now to FIG. 1, the present invention, in certain aspects, is directed to a method and apparatus for reconstituting a bone sample with a biological fluid prior to surgical implantation into a patient. As used herein, "bone sample" includes cadaveric bone grafts from animals, including humans, as well as synthetic bone graft material now known or later developed. The term "bone sample" also includes any other implantation or grafting material amenable to reconstitution with a fluid. The prepared bone sample may be used in surgical procedures on human patients as well as in veterinary surgical procedures.

As shown in FIG. 1, the invention comprises a container 10 having an inner reservoir 11 for holding a fluid F for subsequent reconstitution into a bone sample B. As used herein, "fluid" includes any liquid-based biological fluid (natural or synthetic), such as blood plasma. The blood plasma may contain a high concentration of platelets, growth factors, fibrinogen, and/or other components useful in aiding in bone fusion, for example. An exemplary blood plasma product is that described in the Applicants' co-pending application U.S. Ser. No. 09/994,908, which is incorporated herein by reference in its entirety. The term "fluid" also includes any other solution or suspension, including, but not limited to, saline solutions, dextrose solutions, Ringer's Lactate solutions, and the like. The reservoir 11 includes a closeable port 12 through which ambient air may be drawn through, as discussed further below. Preferably, a stopcock 21 or similar valve device is inserted into the port to regulate the flow of air therein. A Luer lock (not shown) may also be provided within the port to further secure the stopcock within the port. Alternatively, a slidable lid or a simple, non-adjustable stop (not shown) may be placed within the port 12.

The container also includes an inner bone chamber 13 for maintaining the bone sample B. The container may further include an opening 14 through which the bone sample B is inserted. An open passageway communicating between the bone chamber 13 and the reservoir 11 is provided within the container. Preferably, this passageway is an elongated tube 15, as shown in FIG. 1; however, it will be appreciated by the those of ordinary skill in the art that the tube may be of various lengths depending upon the size of the container and the placement of the bone chamber and reservoir with respect to one another. It will be further appreciated by the skilled artisan that the container may be modified such that the bone chamber and reservoir walls are flush with one another or comprise a common, integral structure (not shown), such that the open passageway communicating between the two areas 11, 13 may simply comprise a hole within the wall(s).

The container 10 further includes a vacuum chamber 16 positioned adjacent the bone chamber 13. Connecting the vacuum chamber 16 to the bone chamber 13 is a second open passageway. Again, preferably this passageway is an elongated tube 17 as shown in FIG. 1; however, the tube may be of varying lengths and dimensions as desired. Moreover, the respective vacuum and bone chambers may share a common wall (not shown), such that the passageway is an open hole (not shown) communicating between the two chambers 13, 16. The vacuum chamber 16 includes an external port 18 to which an external vacuum source may be connected. Preferably, the external vacuum source is a conventional syringe 30 as shown. The syringe 30 includes a barrel 31 housing a plunger 32 therein. The distal open end 33 of the syringe is attached to a stopcock 21, preferably a three-way stopcock as shown. The stopcock may be further secured within the vacuum port by means of a Luer lock (not shown), for example. While the syringe system is preferred due to its simplicity and minimal expense, it will be appreciated that the other vacuum devices, such as a motorized vacuum pump, may be utilized instead.

To operate the invention, a bone sample B is placed within the bone chamber 13, and the reconstitution fluid F is placed within the reservoir 11. The reservoir port 12 is then closed by closing the stopcock 20 (when the stopcock is employed). A second stopcock 21 is preferably secured within the vacuum port 18 at one open end 21a of the stopcock. With the plunger 32 pushed all the way down within the barrel of the syringe, the distal end 33 of the syringe is secured to a second open end 21b of the stopcock (it will be recognized that alternatively, the stopcock may be an integral unit of the syringe). With the reservoir port 12 closed, the plunger 32 is then pulled upward (as shown) to create a negative pressure vacuum within the container 10, and more specifically, within the bone chamber 13 and reservoir 11. The reservoir port 12 is then opened to allow ambient air to be drawn into the reservoir 11. Because of the negative pressure vacuum created within the reservoir 11, the ambient air pushes the fluid F through the passageway 15 and into the bone chamber 13 wherein the fluid F is forced into the bone sample B to completely permeate the interstitial spaces within the bone.

Preferably, the vacuum passageway 17 contains an air permeable membrane 40, as better shown in FIG. 2, to prevent the fluid from exiting the bone chamber. Exemplary materials for constructing the membrane include polyester screen or mesh materials typically used in cardiovascular applications, such as blood filters for leukocyte reduction and extracorporeal services, for example.

The dimensions of the syringe 30, the container 10, and the container components illustrated and described herein may be of any size, depending largely upon the size of the bone sample. Exemplary dimensions suitable for many applications include container dimensions of 7 inches (width)×7 inches (height)×1.5 inches (depth), a bone chamber 13 2 inches in width, and a reservoir 11 deep enough to contain about 10 ml of fluid. A preferred syringe size is a 60 ml syringe, the largest syringe size currently available on the market; however, larger sizes may be fabricated for use with the present invention. Also, for added stability of the container during operation, a support footing 50 may be provided as shown to prevent the container from tipping over. Other means for supporting the container may be provided, as well, such as external clamps or brackets (not shown).

The container 10 and its components, including the syringe, may be fabricated out of plastic or similar disposable materials, for example, and discarded after a single use. It will be appreciated that other materials may be employed, however, that will allow for multiple uses of the apparatus.

FIG. 1 illustrates the preferred embodiment of the present invention, wherein the container 10 includes three separate inner chambers or reservoirs (i.e. a reservoir 11 for holding the fluid, a bone chamber 13, and a vacuum chamber 16). Alternatively, the vacuum chamber could be eliminated and instead, the vacuum port 18 be oriented in direct communication with the bone chamber 13. In this embodiment, an air permeable membrane should be provided within the vacuum port, the syringe, or stopcock, to prevent fluid from backing up into the barrel of the syringe.

The preferred embodiment of the inventive apparatus allows for an efficient and rapid method for reconstituting bone samples with fluids via application of a negative pressure vacuum. The vacuum environment within the bone chamber allows the fluid to permeate the entire bone sample. When the fluid employed is plasma containing a high concentration of growth factors, for example, the resulting reconstituted bone sample provides an enhanced rate of bone fusion and growth within the patient post-surgery.

While application of a negative pressure vacuum is preferred due to safety considerations, it will be appreciated by the those of ordinary skill in the art that the bone sample may be reconstituted with the desired fluid via application of a positive pressure. In this embodiment, the syringe would be attached to the reservoir port with the plunger initially pulled away from the distal end after the bone sample and fluid are placed in their respective chamber/reservoir. Air within the barrel of the syringe is then pushed within the reservoir to force the fluid into the bone chamber via the passageway connecting the two. This positive air pressure thereby forces the fluid into the interstices of the bone sample. Instead of the syringe, an external air pump may be employed to create the positive pressure within the container.

We claim:

1. An apparatus suitable for reconstituting a bone sample with a fluid prior to surgical implantation of said bone, said apparatus comprising:

a. a container, said container having an inner reservoir for holding said fluid, an inner bone chamber for holding said bone sample during reconstitution of said bone with said fluid, and an inner vacuum chamber through which a negative pressure vacuum is initially drawn to pull said fluid from said reservoir into said bone sample for subsequent reconstitution of said bone sample;

b. a fluid transport passageway in communication with said reservoir at one end and said bone chamber at another end;

c. a vacuum passageway in communication with said bone chamber at one end and said vacuum chamber at another end;

d. an air permeable membrane secured within said vacuum passageway to prevent said fluid from exiting said bone chamber;

e. said reservoir including a closable port through which ambient air may be drawn into said reservoir upon application of said vacuum within said container; and f. said vacuum compartment further including a port configured for attachment to an external vacuum source, such that when said vacuum is drawn, a negative pressure results within said container such that upon opening of said reservoir port, said fluid is driven into said bone chamber and into said bone sample, thereby reconstituting said bone sample with said fluid.

2. The apparatus of claim 1, wherein said fluid comprises blood plasma.

3. The apparatus of claim 2, wherein said blood plasma comprises a high concentration of growth factors and platelets.

4. The apparatus of claim 1, wherein said fluid is selected from the group of saline solutions, dextrose solutions, and Ringers Lactate solutions.

5. The apparatus of claim 1, wherein said passageways are tubes.

6. The apparatus of claim 1, wherein said fluid is selected from the group of blood plasma, saline solutions, dextrose solutions, and Ringers Lactate solutions.

7. The apparatus of claim 1, wherein said vacuum source comprises:

a. a stopcock having at least three closeable openings, said stopcock secured to said vacuum compartment port at one of said openings;

b. a syringe, said syringe further having a hollow barrel, a plunger movably housed within said barrel, and a distal open end configured for attachment to a second opening of said stopcock.

8. The apparatus of claim 7, wherein said passageways are tubes.

9. An apparatus suitable for reconstituting a bone sample with a fluid prior to surgical implantation of said bone, said apparatus comprising:

a. a container having an inner reservoir for holding said fluid, an inner bone chamber for holding said bone sample during reconstitution of said bone with said fluid, and an inner vacuum chamber through which a negative pressure vacuum is initially drawn to pull said fluid from said reservoir into said bone sample for subsequent reconstitution of said bone sample;

b. a fluid transport tube in communication with said reservoir at one end and said bone chamber at another end;

c. a vacuum rube in communication with said bone chamber at one end and said vacuum chamber at another end;

d. an air permeable membrane secured within said vacuum tube to prevent said fluid from exiting said bone chamber;

e. said reservoir including a closable port through which ambient air may be drawn into said reservoir upon application of said vacuum within said container; and f. said vacuum compartment further including a port configured for attachment to an external vacuum source, such that when said vacuum is drawn, a negative pressure results within said container such that upon opening of said reservoir port, said fluid is drawn into said bone chamber and into said bone sample, thereby reconstituting said bone sample with said fluid.

10. The apparatus of claim 9, wherein said vacuum source comprises:

a. a stopcock having at least three closeable openings, said stopcock secured to said vacuum compartment port at one of said openings; and b. a syringe, said syringe further having a hollow barrel, a plunger movably housed within said barrel, and a distal open end configured for attachment to a second opening of said stopcock.

11. The apparatus of claim 10, wherein said reservoir includes a locking device secured within said reservoir port for maintaining a second stopcock within said port.

12. The apparatus of claim 9, wherein said fluid comprises blood plasma.

13. The apparatus of claim 12, wherein said plasma comprises a high concentration of growth factors.

14. The apparatus of claim 9, wherein said fluid is selected from the group of saline solutions, dextrose solutions, and Ringers Lactate solutions.

15. The apparatus of claim 9, wherein said reservoir includes a locking device secured within said reservoir port for maintaining a second stopcock within said port.

16. An apparatus suitable for preparing bone samples for subsequent surgical implantation, said apparatus comprising:

a. a container having an inner reservoir for holding biological fluid intended for reconstitution with said bone sample, an inner bone chamber for holding said bone sample during said reconstitution, and an inner vacuum chamber through which a negative pressure vacuum is initially drawn to pull said fluid from said reservoir into said bone sample;

b. a fluid transport tube in communication with said reservoir at one end and said bone chamber at another end;

c. a vacuum tube in communication with said bone chamber at one end and said vacuum chamber at another end;

d. an air permeable membrane secured within said vacuum tube to prevent fluid from exiting said bone chamber;

e. a vacuum source configured for attachment to said container;

f. said reservoir including a closable port through which ambient air may be drawn into said reservoir upon application of said vacuum within said container; and g. said vacuum compartment further including a port configured for attachment to said vacuum source, such that when said vacuum is drawn, a negative pressure results within said container such that upon opening of said reservoir port, said fluid is drawn into said bone chamber and forced into said bone sample, thereby reconstituting said bone sample with said fluid.

17. The apparatus of claim 16, wherein said vacuum source comprises:

a. a stopcock having at least three closeable openings, said stopcock secured to said vacuum compartment port at one of said openings; and b. a syringe, said syringe further having a hollow barrel, a plunger movably housed within said barrel, and a distal open end configured for attachment to a second opening of said stopcock.

* * * * *